United States Patent [19]

Suzuki

[11] Patent Number: 4,870,951
[45] Date of Patent: Oct. 3, 1989

[54] ENDOSCOPE HAVING VARYING DIAMETER CONTENTS IN THE INSERTABLE PART

[75] Inventor: Akira Suzuki, Hachioji, Japan
[73] Assignee: Olympus Optical Co., Ltd., Tokyo, Japan
[21] Appl. No.: 222,590
[22] Filed: Jul. 21, 1988
[30] Foreign Application Priority Data Aug. 4, 1987 [JP] Japan ................................. 62-195902
Aug. 18, 1987 [JP] Japan ........................... 62-126236[U]

[51] Int. Cl.⁴ ............................................... A61B 1/06
[52] U.S. Cl. ............................................ 128/6; 128/4
[58] Field of Search .......................... 128/4, 6; 258/98

[56] References Cited

U.S. PATENT DOCUMENTS

| 4,351,323 | 9/1982 | Ouchi et al. | 128/4 |
| 4,618,884 | 10/1986 | Nagasaki | 258/98 |
| 4,745,908 | 5/1988 | Wardle | 128/6 |
| 4,794,912 | 1/1989 | Lia | 128/4 |

*Primary Examiner*—William H. Grieb
*Attorney, Agent, or Firm*—Armstrong, Nikaido, Marmelstein, Kubovcik & Murray

[57] ABSTRACT

This endoscope is provided with an elongate insertable part having an observing window in the tip part and an observing system for observing an object by receiving a light entering through the observing window and is further provided with contents which are contained within the insertable part and at least one of which varies in the outside diameter so as to be smaller in the diameter on the rear end side, driven parts provided in the insertable part and driving parts driving the driven parts and arranged to be closer to the rear end side than the position in which the contents vary in the outside diameter. The contents are, for example, an image guide and light guide coated with protective tubes in the curvable part. The driven parts are, for example, a curvable part and treating tool raising device provided in the insertable part. Alternatively, the endoscope is provided with an insertable part, an observing system, a curvable part provided in the inserting part and a plurality of driving devices provided within the insertable part and driving the curvable part so as to be curved. At least one of the driving devices is arranged in a different position in the axial direction of the insertable part from the other driving devices.

22 Claims, 9 Drawing Sheets

ENDOSCOPE HAVING VARYING DIAMETER CONTENTS IN THE INSERTABLE PART

BACKGROUND OF THE INVENTION

1. Field of the Invention

This invention relates to an endoscope having a driving means driving a curvable part and treating tool raising device within an insertable part.

2. Related Art Statement

Recently, there is extensively used an endoscope whereby an organ within a body cavity can be observed by inserting an elongate insertable part into the body cavity or, as required, various curing treatments can be made by using treating tools inserted through a treating tool channel.

Now, in the above mentioned endoscope, a curvable part curvable on the tip side is provided in the insertable part so as to be operatable to be curved. There is a means of operating the above mentioned curvable part wherein a curving operation knob is provided in the operating part and is rotated and operated or wherein such driving means as a motor is provided near the curvable part.

A small endoscope simplified in the structure and provided with a driving means such as a vibration wave motor near the curvable part of the insertable part is shown, for example, in the publication of a Japanese patent application laid open No. 106126/1986. There are advantages that, when the driving means is thus provided near the curvable part, the response to the curving operation will be higher, the inspection will be able to be made with the minimum operation and the pain of the patient will be able to be reduced.

On the other hand, the curvable part will be curved in use so frequently as to be more likely to damage the contents than the other parts of the insertable part. Therefore, within the curvable part, the contents are covered with a protective tube to prevent damage.

Now, the length of the contents protecting tube provided within the curvable part is so set that the protecting tube end surface may come closer to the operating part side than the connecting piece of the articulated frame at the rearmost end.

Also, the contents within the insertable part are packed as much as possible so as to make the outside diameter of the insertable part as fine as possible to reduce the pain of the patient.

The vibration wave motor driving part is larger in outside diameter than the driving power transmitting part and requires a larger space.

Therefore, if the driving part is arranged in position in which the area occupied by the contents within the insertable part is maximum such as in the part covered by the above mentioned protecting tube, the insertable part will have to be made larger in outside diameter by an amount equal to the difference between the cross-sectional area of the driving part and the cross-sectional area of the driving power transmitting part so that the pain of the patient will become larger.

In an endoscope provided with a treating tool raising device in the tip part of the insertable part, it is considered to provide a driving means such as a vibrating wave motor within the insertable part as a means of driving this treating tool raising device. In such a case, too, if the above mentioned driving means is arranged in the position in which the area occupied by the contents within the insertable part is maximum, the insertable part will become larger in outside diameter.

In the above mentioned related art example, four wire driving parts are provided as curving driving means and are arranged in the same positions in the position relation in the axial direction of the insertable part. Therefore, there are four wire driving parts in the cross-sectional area of the insertable part including the above mentioned wire driving parts. As this wire driving part is larger in outside diameter than the drive transmitting part, the outside diameter of the insertable part will be determined by the sum of the sizes of the four wire driving parts and the size of the other contents contained in the part in which these wire driving parts exist. Therefore, there are problems that, if the four wire driving parts exist in the same crosssection, the insertable part will become larger in outside diameter and the pain of the patient will become larger.

OBJECT AND SUMMARY OF THE INVENTION

An object of the present invention is to provide an endoscope wherein a driving device is provided within the insertable part to prevent the insertable part from having a large outside diameter.

Another object of the present invention is to provide an endoscope wherein, even if a plurality of driving device are provided within the insertable part, the outside diameter of the insertable part will be able to be prevented from becoming larger.

The endoscope of the present invention is provided with an elongate insertable part having an observing window in the tip part and an observing for observing an object by receiving a light entering through the above mentioned observing window. The endoscope is further provided with contents which are contained within the above mentioned insertable part and at least one of which varies in outside diameter so as to be small on the rear end side. Driven parts are provided in the above mentioned insertable part and a driving device drives these driven parts and arranged closer to the rear end side than the position in which the outside diameter of the above mentioned contents varies. The above mentioned contents are, for example, an image guide and light guide covered with protective tubes in the curvable part. The above mentioned driven parts are, for example, a curvable part and treating tool raising device provided in the insertable part. Or the endoscope is provided with the above mentioned insertable part, above mentioned observing device, a curvable part provided in the above mentioned insertable part and a plurality of driving device provided within the above mentioned insertable part and driving the above mentioned curvable part so as to be curved. At least one of the driving device is arranged in a different position in the axial direction of the insertable part from the position of the other driving means.

The the features and advantages of the present invention will become apparent enough with the following explanation.

BRIEF DESCRIPTION OF THE DRAWINGS

FIGS. 1 to 8 relate to the first embodiment of the present invention.

FIGS. 9 to 11 relate to the second embodiment of the present invention.

FIGS. 12 to 16 relate to the third embodiment of the present invention.

FIGS. 17 to 19 relate to the fourth embodiment of the present invention.

DETAILED DESCRIPTION OF PREFERRED EMBODIMENTS

FIGS. 1 to 8 show the first embodiment of the present invention.

Figure 2:
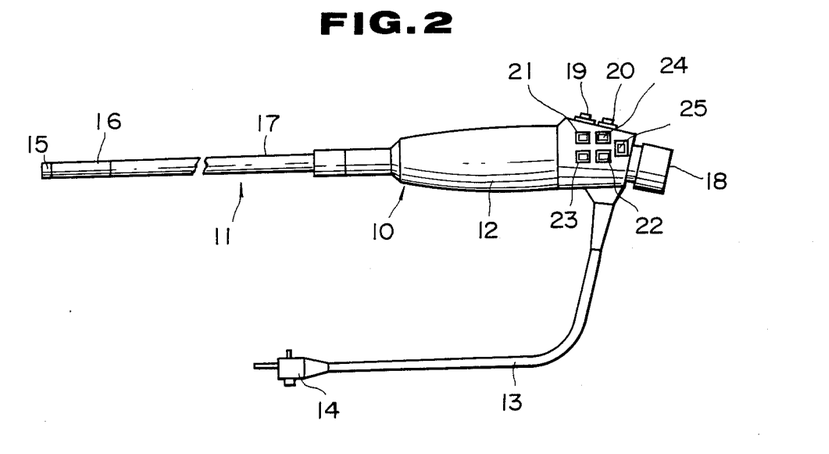
FIG. 2 is a side view of an endoscope.

As shown in FIG. 2, an endoscope 10 is provided with an elongate flexible insertable part and an operating part 12 connected to this insertable part at the base end. A flexible universal cord 13 is extended from the above mentioned operating part 12 and is provided at the tip with a connector 14. The above mentioned insertable part 11 is formed of a tip part 15, curvable part 16 and flexible tube part 17 in the order mentioned from the tip side. The above mentioned operating part 12 is connected at the rear end with an eyepiece part 18 and is provided on the side with an air and water feeding switch 19, suction switch 20, curving operation switches 21 (down), 22 (up), 23 (left) and 24 (right) and switching switch 25 switching an angle to be locked/-free.

Figure 1:
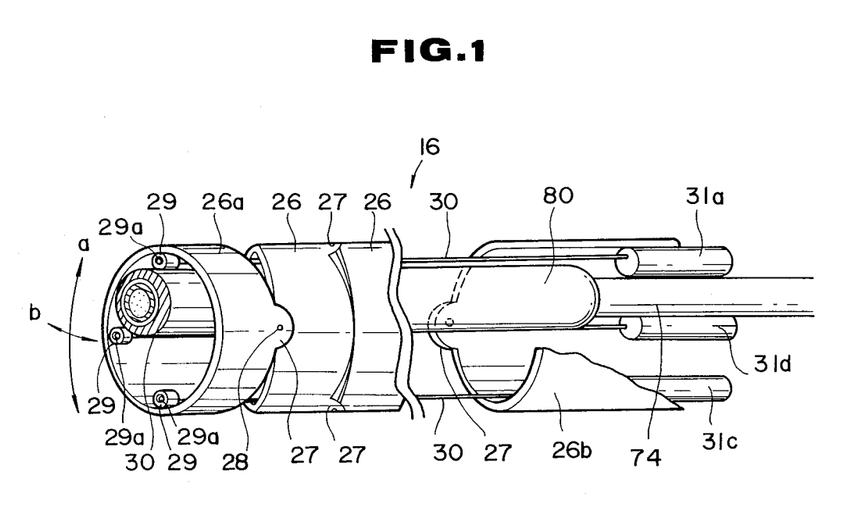
FIG. 1 is a perspective view showing the vicinity of a curvable part.
Figure 3:
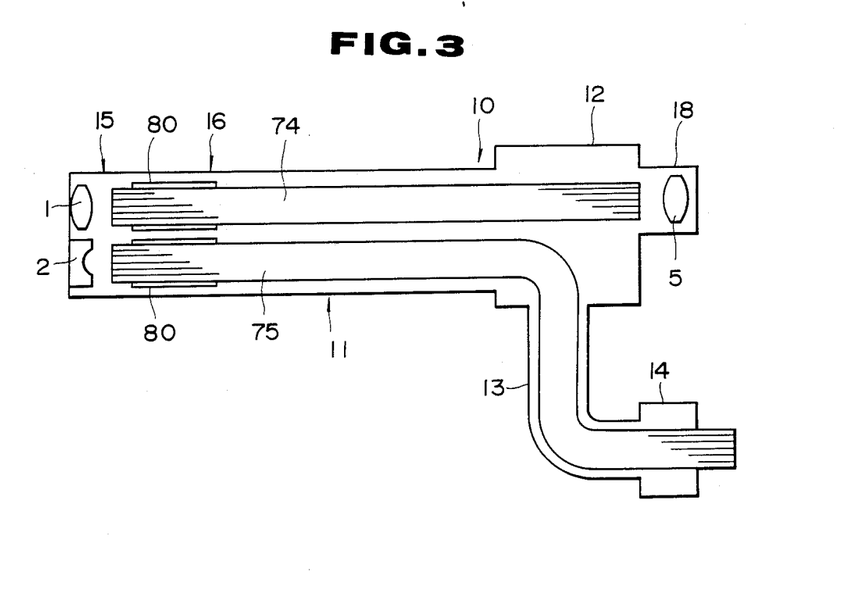
FIG. 3 is an explanatory view showing the formation of the endoscope.

As shown in FIG. 3, the above mentioned tip part 15 is provided with an objective lens system 1 and light distributing lens 2. A light guide 75 is connected to the above mentioned light distributing lens 2 on the rear end side, is inserted through the above mentioned insertable part 1 and universal cord 13 and is connected to the above mentioned connector 14. When this connector 14 is connected to a light source apparatus (not illustrated), an illuminating light from this light source apparatus will enter the above mentioned light guide 75 at the entrance end, will be led to the tip part 15 by the above mentioned light guide 75, will be emitted from the tip of this light guide 75 and will be radiated to an object through the light distributing lens 2. The tip surface of an image guide 74 is arranged in the image forming position of the above mentioned objective lens system 1. As shown in FIG. 1, this image guide 74 is inserted through the above mentioned insertable part 11 and is extended to the above mentioned eyepiece part 18 side. The object image formed on the tip surface of the above mentioned image guide 74 by the above mentioned objective lens system 1 will be transmitted to the eyepiece part 18 side by this image guide and will be observed through the eyepiece lens 5 from this eyepiece part 18.

As shown in FIG. 1, the above mentioned curvable part 16 is formed of articulated frames 26 consisting of many short cylindrical tubular bodies as connected rotatably in the vertical direction indicated by the arrow a and in the horizontal direction indicated by the arrow b. That is to say, respective pairs of connecting pieces 27 are provided to project as displaced by 180 degrees in the peripheral direction from both end surfaces of respective articulated frames 26 and as displaced by 90 degrees in the peripheral direction on both end surfaces and respective pairs of connecting pieces 27 of the adjacent articulated frames 26 are pivotally jointed respectively by pivots 28. The connecting pieces 27 are provided to project only on one end surface of each of articulated frames 26a and 26b respectively at the tip and rearmost end of the curvable part 16. Therefore, the curvable part 16 made of the articulated frames 26 as thus connected is bendable in the vertical direction indicated by the arrow a and in the horizontal direction intersecting at right angles with this vertical direction and indicated by the arrow b.

Cylindrical wire fixing parts 29 are provided respectively in four places displaced by 90 degrees in the peripheral direction corresponding to the curving direction of the curvable part on the inner peripheral surface of the articulated frame 26a at the foremost end. A curving wire 30 is inserted at one end into a through hole 29a in each wire fixing part 29 and is firmly secured as by soldering. Four curving wires 30 are pulled respectively at the other ends through four wire driving parts 31a, 31b, 31c and 31d as a curving driving means provided respectively as displaced by 90 degrees on the inner peripheral surface of the articulated frame 26b (only 31b is not illustrated) so that the articulated frames 26 may be curved and driven by the curving wires 30 and wire driving parts 31 (representing 31a, 31b, 31c and 31d).

The above mentioned image guide 74 is contained within the insertable part 11 and is coated with a protective tube 80 so as to be prevented from being damaged within the curvable part 6. The entire length of this protective tube 80 is set so that the rear end of the protective tube 80, when the curvable part 16 is curved freely, may be closer to the operating part 12 side than the connecting piece 27 of the articulated frame 26b at the rearmost end. Further, the wire driving parts 31 are as arranged as to secure a distance in the axial direction from the rear end of the protective tube 8 when the curvable part 16 is curved freely. That is to say, the above mentioned wire driving part 31 is arranged to be closer to the operating part 12 side than the position in which the outside diameters of the image guide 74 and protective tube 80 become smaller.

Though not shown in FIG. 1, not only the above mentioned image guide 74 but also the light guide 75 and air and water feeding channel tube are inserted in the above mentioned insertable part 11 and are coated as required with the protective tubes 80 within the above mentioned curvable part 16.

Figure 4:
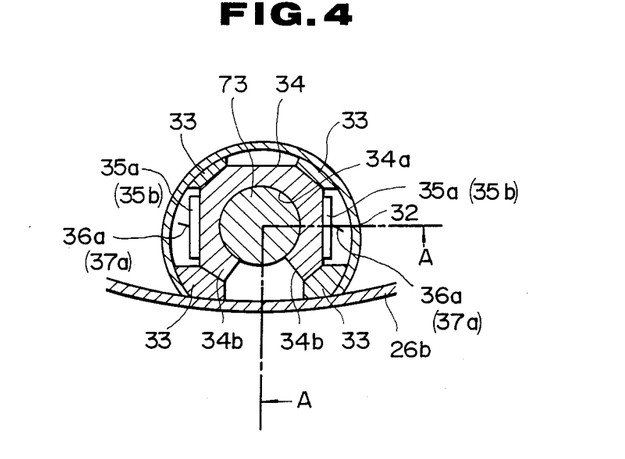
FIG. 4 is vertically sectioned view of a wire driving part.

As shown in FIG. 4, the outer fitting part 32 of the wire driving part 31a is formed of a cylindrical pipe member provided on the inner peripheral surface with four fixing members 33 over the entire length in the axial direction as separated by substantially 90 degrees in the peripheral direction. These fixing members 33 support and fix from four directions a fitting member 34 consisting of an elastic vibrator. The fitting member 34 has substantially the same length as the length in the axial direction of the outer fitting part 32 and its cross-section in the peripheral direction is substantially channel like. That is to say, a fitting groove 34a is provided in the axial direction. Two arms 34b of the fitting member 34 are somewhat inclined inward, that is, toward each other so as to hold from both sides a connecting rod 73 connected, for example, by soldering to the curving wires 30. In the natural state, the inside diameter of the fitting groove 34a is slightly smaller than the outside diameter of the connecting rod 73 but, in the fitted state, the connecting rod 73 is fixed in close contact with the inner peripheral surface of the fitting groove 34.

Figure 5:
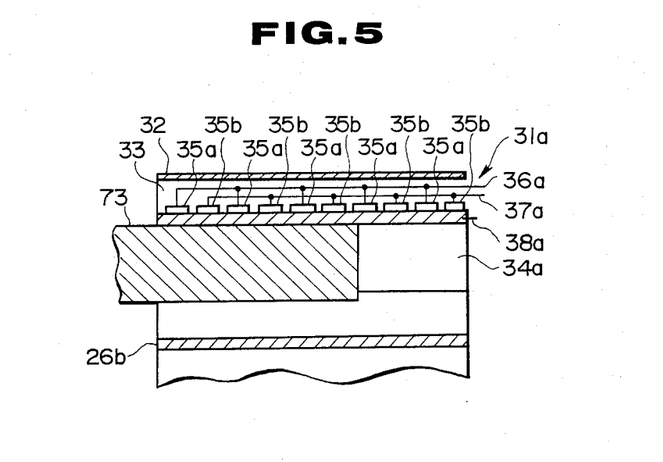
FIG. 5 is a sectioned view on line A—A in FIG. 4.

As shown in FIG. 5, many electrostrictive elements 35a and 35b are respectively alternately bonded in the axial direction at the intervals most adapted to generate later described fixed vibration waves on two opposed planes provided on the outer periphery of the fitting member 34. The electrostrictive elements 35a and 35b are connected respectively to electric wires 36a and 37a. An electric wire 38a is connected to the fitting member 34. The other wire driving parts 31b, 31c and 31d are also similarly formed and shall not be explained.

Figure 6:
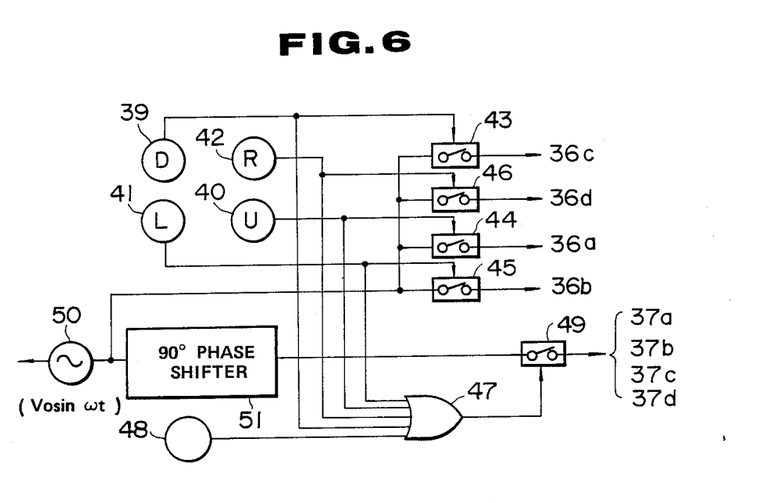
FIG. 6 is a circuit diagram showing a drive controlling circuit of the wire driving part.

A controlling circuit as a controlling means controlling the respective wire driving parts 31 shall be explained with reference to FIG. 6. Switch controlling circuits 39 to 42 provided to correspond respectively to the curving operation switches 21 to 24 are operatively connected to the respective switches to be on/off to output high level (H)/low level (L) voltages. The respective switch controlling circuits 39 to 42 are connected at the respective output ends to switch boxes 43 to 46 at the controlling input ends and are connected to an OR circuit 47 at the input end.

A switch controlling circuit 48 provided to correspond to the switching switch 25 outputs an H level voltage by an angle free operation and L level voltage by an angle locked operation and is input at the output end into the OR circuit 47 at the input end. The OR circuit 47 is connected at the output end to a switch box 29 at the controlling input end.

A driving power source 50 feeds a voltage $V=V_0 \sin \omega t$, is connected at one end to the above mentioned electric wires 38a to 38d and at the other end to a 90-degree phase shifter 51 at the input end and is connected to switch boxes 43 to 46 at the respective input ends. The switch boxes 43, 46, 44 and 45 are connected at the output ends respectively to the above mentioned electric wires 36c, 36d, 36a and 36b. The 90-degree phase shifter 51 advances or delays by 90 degrees the phase of the input voltage and is connected at the output end to the switch box 49 at the input end. The switch box 49 is connected at the output end to the above mentioned electric wires 37a to 37d. The switch boxes 43 to 46 and 49 will conduct at the input ends and output ends when the voltage at the controlling input end is on an H level but will disconnect the conduct when it is on an L level.

Here, the operating principle of the vibration wave motor (also called a piezoelectric motor or ultrasonic wave motor) formed of the fitting member 34 of the above mentioned wire driving part, the connecting rod 73 connected to the curving wires 30 and the electrostrictive elements 35a and 35b shall be explained, for example, with the above mentioned wire driving part 31a.

Figure 7:
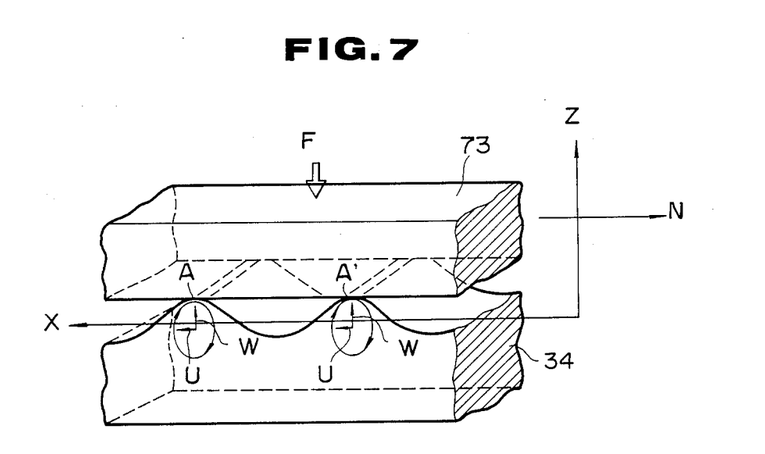
FIG. 7 is an explanatory view showing the driving principle of a vibration wave motor used in the wire driving part.

In FIG. 7, the reference numeral 73 typically represents the connecting rod as a pressed mover and 34 typically represents the fitting member as a stator elastically vibrated by the electrostrictive element (such as, for example, PZT) as an electric-mechanical energy converting means. The X-axis represents the direction on the surface of the stator 34 and the Z-axis represents the normal direction of the same. When a bending vibration is given to the surface of the stator 34 by the electrostrictive elements, a progressing vibration wave will be generated and will be propagated on the surface of the stator 34. This progressing vibration wave is a surface wave accompanied by a vertical wave and horizontal wave and the motion of its material point describes an elliptic orbit. It is noted that the material point A makes an elliptic motion of a vertical amplitude u and horizontal amplitude w. When the progressing direction of the surface wave is the X-axis direction, the elliptic motion will be in the clockwise direction. This surface wave has apexes A, A'—in the respective wavelengths and its apex velocity is only of the X component and is $v=2\pi n f u$ (where f is a number of vibrations). Therefore, when the surface of the mover 73 is frictionally contacted with the surface of the stator 34, the surface of the mover 73 will contact only the apexes A, A'—and therefore the mover 73 will be driven in the direction indicated by the arrow N by the friction force.

The velocity of the mover 73 is proportional to the number f of vibrations and depends on not only the vertical amplitude u but also the horizontal amplitude w due to the friction drive by the pressure contact. That is to say, the velocity of the mover 73 is proportional to the magnitude of the elliptic motion. Therefore, the velocity of the mover 73 is proportional t the voltage applied to the electrostrictive elements.

Figure 8:
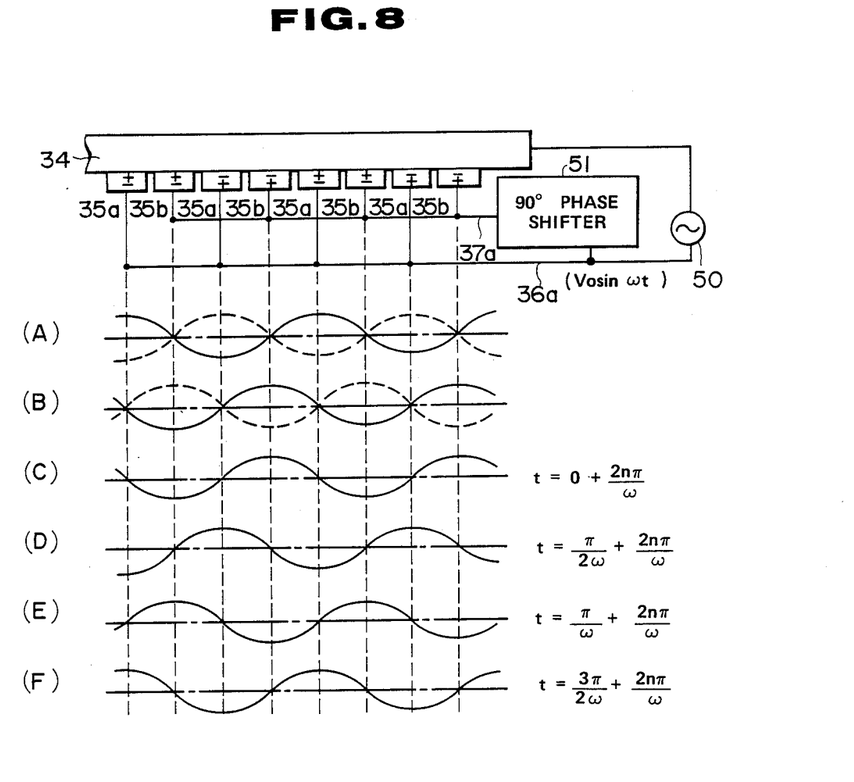
FIG. 8 is an explanatory view showing the generation of progressing vibration waves and fixed vibration waves in a vibration wave motor.

FIG. 8 is a view for explaining the generation of progressing vibration waves and fixed vibration waves. When the electrostrictive elements 35a and 35b operate alone, the stator 34 will be arranged so as to resonate, that is, to be in the position in which fixed vibration waves exist and so that the fixed vibration wavelength by the electrostrictive element 35a and the fixed vibration wavelength by the electrostrictive element 35b may be equal to each other and the phase may be displaced by 90 degrees (the physical position may be displaced by ¼ wavelength). The driving power source 50 will feed a voltage of $V=V_0 \sin wt$. The voltage of $V_0 \sin wt$ will be applied to the electrostrictive element 35a directly from the driving power source 50 by a line 36a. A voltage of $V_0 \sin (wt \pm \pi/2)$ will be applied to the electrostrictive element 35b through a 90-degree phase shifter 51 by the line 37a. The ± of the voltage $V_0 \sin (wt \pm \pi/2)$ will be switched by the direction of moving the mover 73. (A) to (F) in FIG. 8 show the states of the vibration waves in case the voltage $V_0 \sin (wt \pm \pi/2)$ is being applied. (A) shows the state that fixed vibration waves are being generated by the electrostrictive element 35a only. (B) shows the state that fixed vibration waves having a 90-degree phase advance are being generated by the electrostrictive element 35b only. (C) to (F) show the state that progressing vibration waves are being generated by simultaneously operating the two electrostrictive elements 35a and 35b. (C) shows the phase of the progressing vibration waves at a time of $t=0+2n\pi/w$, (D) shows the phase of the progressing vibration waves at a time of $t=n/w+2n\pi/w$ and (F) shows the phase of the progressing vibration waves at a time of $t=3n/2w+2n\pi/w$. The progressing vibration waves will progress leftward in FIG. 8 but any material point on the frictional contact surface of the stator 34 will make a clockwise elliptic motion. Therefore, the mover 73 will move rightward.

In the fixed vibration generating states of (A) and (B), at the other material points than the knots on the frictional contact surface of the stator 34, there are only horizontal vibrations, that is, vertical motions in FIG. 8. Therefore, the frictional contact between the mover 73 and stator 34 will not be in a stationary frictional state but will be in a moving frictional state, therefore coefficient of friction will become smaller and the contact area will also become smaller. Therefore, the mover 73 will be able to be easily moved by an external force.

The operation of this embodiment shall be explained in the following. First of all, the case of angle-locking the switching switch 25 shall be explained with the case of operating the curvable part to be up as an example. When the curving operation switch 22 (up) is switched ON, the switch controlling circuit 40 will output an H level signal and therefore the switch boxes 44 and 49 will conduct at the respective input and output ends. As a result, a voltage of $V = V_0 \sin \omega t$ will be fed to the electric wire 36a and a voltage of $V = V_0 \sin(\omega t + \pi/\omega)$ will be fed to the electric wires 37a to 37d but no voltage will be fed to the electric wires 36b to 36d. Therefore, fixed vibration waves will be generated in the fitting member 34 consisting of the elastic vibrators of the driving parts 31b to 31d and the fitting member 34 will become easily movable by an external force. On the other hand, progressing vibration waves in the direction of pulling the wire 30 connected to the connecting rod 73 will be generated in the fitting member 34 of the wire driving part 31a. Therefore, when the wire 30 is pulled in the UP direction, the curvable part will be smoothly curved in the UP direction. When the curving operation switch 22 is switched OFF, no voltage will be applied to the fitting member of each wire driving part 31, therefore the curvable part will stop as curved and will not be easily moved even if an external force is applied to it. In the same manner, if the curving operation switches 21, 23 and 24 are switched ON, the curvable part will curve respectively in the DOWN, LEFT and RIGHT directions but the explanation shall be omitted.

In case the switching switch 25 is operated to be anglefree, the switch controlling circuit 48 will output an H level signal and therefore the switch box 49 will be conductive at the input and output ends. Therefore, as the voltage of $V = V_0 \sin(\omega t + \pi/2)$ is always applied to the fitting member 34 of each wire driving part 31, fixed vibration waves will be always generated. In this state, for example, if the curving operation switch 22 is switched ON, the curvable part will curve in the UP direction the same as in the above described angle-locking operation.

When the curvable part is curved, the protective tube 80 of the image guide 74 will be pulled toward the tip but will not be moved at the rear end toward the tip by the connecting piece 27 of the articulated frame 26b at the rearmost end. In case the curvable part 16 and flexible tube part 17 are made in any form, when the protective tube 80 of the image guide 74 is moved in the axial direction, the wire driving part 31 will not interfere with the protective tube 80.

Thus, in this embodiment, the wire driving part 31 consisting of a vibration wave motor is provided on the rear end side of the curvable part 16 so that the curvable part 16 may be curved and driven by this wire driving part 31. The image guide 74 and others are contained within the insertable part 11. The image guide 74 within the above mentioned curvable part 16 is coated with the protective tube 80 so as to be prevented from being damaged. Therefore, the above mentioned image guide 74 and protective tube 80 are made thicker within the curvable part 16.

In this embodiment, the above mentioned wire driving part 31 is arranged as freely curved with a distance secured in the axial direction from the rear end of the protective tube 75. That is to say, the above mentioned wire driving part 31 is arranged to be closer to the operating part 12 than the position in which the image guide 74 and protective tube 80 become smaller in outside diameter. Therefore, as the thick part of the image guide 74 coated with the protective tube 80 and the wire driving part 31 do not exist as overlapped in any cross-section in the axial direction of the insertable part 11, the maximum content area of the insertable part 11 will be smaller than in the case of providing the above mentioned wire driving part 31 so as to overlap with the above mentioned protective tube 80 in the rear end part of the curvable part 16 and the insertable part 11 will be able to be made with a small outside diameter.

In the above explanation, the image guide 74 coated with the protective tube 80 has been explained as a content varying in outside diameter. However, it is needless to say that such contents varying in outside diameter may be the light guide 75 coated with the protective tube 80 and the air and water feeding channel tube as shown in FIG. 3.

The present invention is not limited to the above mentioned embodiment. For example, within the curvable part 16, the protective tube protecting the contents of the insertable part 11 is not limited to individually coat the image guide 74 or light guide 75 but may coat all the contents together.

Also, in the above mentioned embodiment, the UP, DOWN, LEFT and RIGHT wire driving parts are simultaneously locked but the UP and DOWN driving parts and LEFT and RIGHT driving part may be separately switched.

When the wire driving parts are provided on both sides of the tip forming part and base operating part so as to pull the curving wires with each other to curve the curvable part, the curvable part will be able to be quickly curved. The electrostrictive element may be provided on the connecting rod (mover) side instead of being provided on the fitting member (stator). A magnetostrictive element may be used instead of the electrostrictive element. If a proper number of the curvable parts of the above mentioned embodiment are provided in proper places of the insertable part of the endoscope so as to be separately operated, a complicated curvature will be able to be made.

As explained above, according to this embodiment, there is an effect that, as the curving driving means is arranged to be closer to the operating part than the position in which the contents of the insertable parts vary to be smaller in outside diameter on the operating part side, even if the curving driving means is provided in the insertable part, the insertable part will be able to be prevented from having outside diameter.

Figure 9:
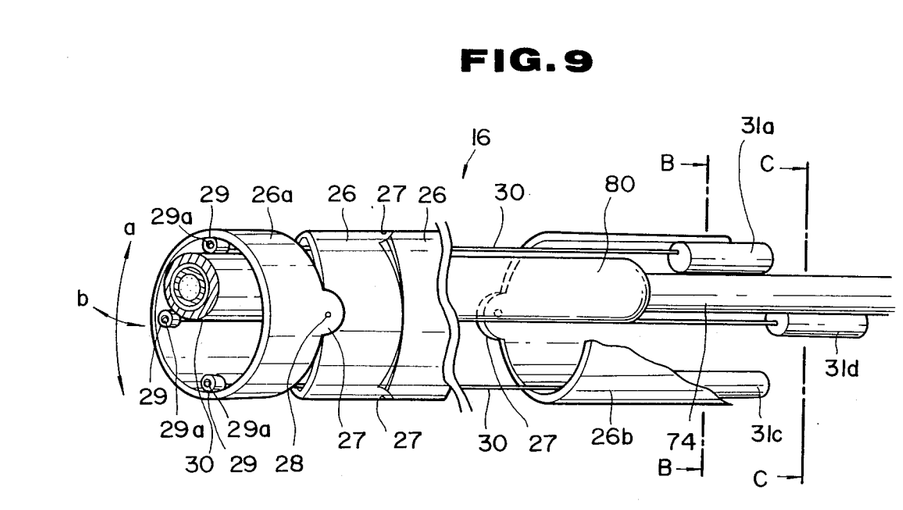
FIG. 9 is a perspective view showing the vicinity of a curvable part.
Figure 10:
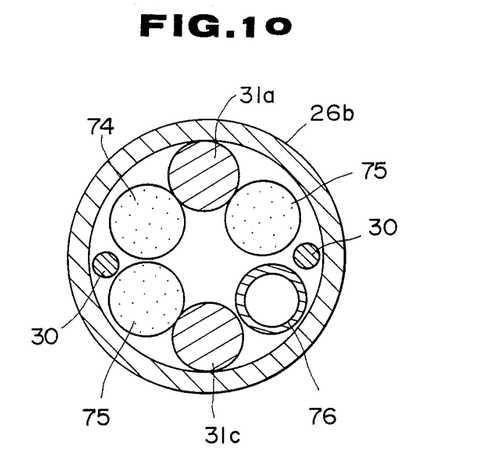
FIG. 10 is a sectioned view on line B—B in FIG. 9.
Figure 11:
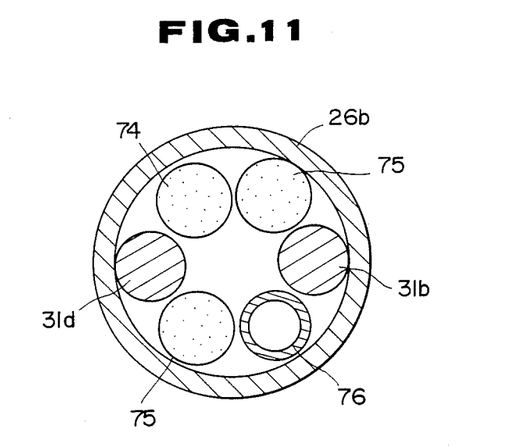
FIG. 11 is a sectioned view on line C—C in FIG. 9.

FIGS. 9 to 11 show the second embodiment of the present invention.

In this embodiment, an objective lens system 1 and, for example, a pair of light distributing lenses 2 are provided in the tip part 15. Light guides 75 such as are shown in FIGS. 10 and 11 are provided on the rear end side of the above mentioned light distributing lenses 2. These light guides 75 are inserted through an insertable part 11 and universal cord 13, are made integral and are connected to a connector 14.

Also, as shown in FIGS. 10 and 11, a suction tube path 76 is inserted through the above mentioned insertable part 11, is inserted through the universal cord 13 and is connected to the connector 14.

Now, in this embodiment, as shown in FIG. 9, the LEFT and RIGHT wire driving parts 31b and 31d among four wire driving parts 31a, 31b, 31c and 31d are arranged to be closer to the operating part 12 side than the UP and DOWN wire driving parts 31a and 31c so as not to be overlapped with the UP DOWN wire driving parts 31a and 31c. Therefore, as shown in FIGS. 10 and 11, the number of the wire driving parts 31 contained in any cross-section of the insertable part 11 is two or less. Other contents in the insertable part 11 than the above mentioned wire driving parts 31 as the above mentioned image guide 74, light guides 75 and suction tube path 76 are contained within articulated frames 36a so as to snake to avoid the above mentioned wire driving parts 31. For example, the image guide 74 and light guides 75 passing on both sides of the front side wire driving part 31a as shown in FIG. 10 are arranged in a hollow space on the operating part 12 side of the front side wire driving part 31a to avoid the rear side wire driving parts 31b and 31d as shown in FIG. 11 on the rear side of the above mentioned wire driving part 31a. In the same manner, the light guides 75 and suction tube path 76 passing on both sides of the front side wire driving part 31c are arranged in a hollow space on the operating part 12 side of the front side wire driving part 31c to avoid the rear side wire driving parts 31b and 31d on the rear side of the above mentioned wire driving part 31c.

The above mentioned image guide 74 is contained within the insertable part 11 and, the same as in the first embodiment, the image guide 74 within the curvable part 16 is coated with a protective tube 80 so as to be prevented from being damaged. This protective tube 80 is set in the entire length so as to be closer to the operating part 12 side than the connecting piece 27 of the articulated frame 26b at the rearmost end. Also, the front side wire driving parts 31a and 31c are arranged with a distance secured in the axial direction from the rear end of the protective tube 80 as freely curved. That is to say, the above mentioned wire driving part 31 is arranged to be closer to the operating part 12 side than the position in which the image guide 74 and protective tube 80 become smaller in outside diameter. Therefore, as the thick part of the image guide coated with the protective tube 80 and the wire driving part 31 are not overlapped with each other in any cross-section in the axial direction of the insertable part 11, the insertable part 11 will be able have a small outside diameter.

The other formations are the same as in the first embodiment.

Thus, in this embodiment, four wire driving parts 31 consisting of vibration wave motors are provided on the rear end side of the curvable part 16 to curve and drive the curvable part 16. Not only the above mentioned wire driving part 31 but also contents such as the image guide 74, light guides 75 and suction tube path 76 are contained within the insertable part.

In this embodiment, the LEFT and RIGHT wire driving parts 31b and 31d of the above mentioned four wire driving parts 31 are arranged to be closer to the operating part 12 side than the UP and DOWN wire driving parts 31a and 31c so as not to overlap with the UP and DOWN wire driving parts 31a and 31c. Therefore, the number of the wire driving parts 31 contained in any cross-section of the insertable part 1 is two or less. The above mentioned image guide 74, light guides 75 and suction tube path 76 are contained within the articulated frames 36b so as to snake to avoid the above mentioned wire driving parts 31 and to effectively utilize the hollow space on the operating part 12 side of the wire driving parts 31.

Therefore, the maximum cross-sectional area of the contents within the insertable part 12 will be smaller than in the case that all the wire driving parts 31 are arranged in the same positions in the axial direction of the insertable part 12. As a result, the insertable part 12 can be made reasonably small in outside diameter and pain to the patient can be reduced.

The other operations and effects are the same as in the first embodiment.

FIGS. 12 to 16 show the third embodiment of the present invention.

Figure 12:
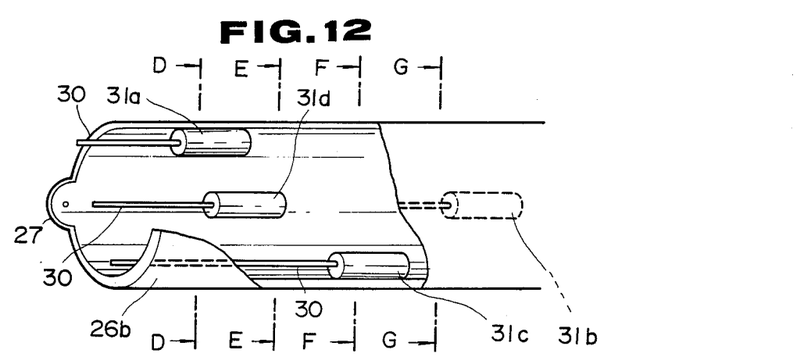
FIG. 12 is a perspective view showing the vicinity of a curvable part.
Figure 13:
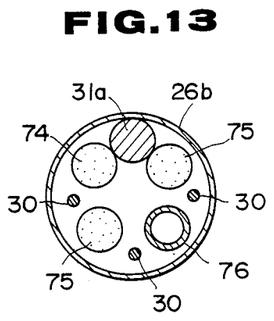
FIG. 13 is a sectioned view on line D—D in FIG. 12.
Figure 14:
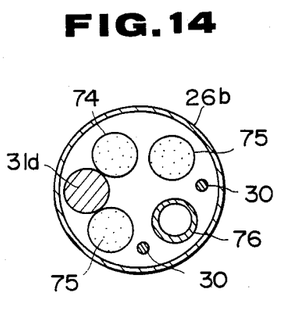
FIG. 14 is a sectioned view on line E—E in FIG. 12.
Figure 15:
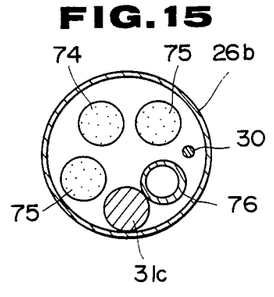
FIG. 15 is a sectioned view on line F—F in FIG. 12.
Figure 16:
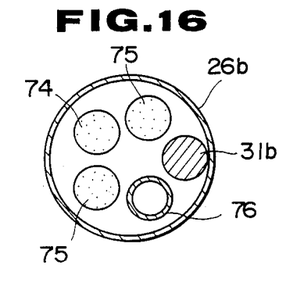
FIG. 16 is a sectioned view on line G—G in FIG. 12.

In this embodiment, as shown in FIG. 12, four wire driving parts 31 are arranged respectively in different positions in the axial direction of the insertable part 11. That is to say, from the front side, for example, the wire driving parts 31a, 31d, 31c and 31b are arranged in, the order mentioned so as not to overlap with each other. Other contents such as the image guide 74, light guides 75 and suction tube path are contained within the articulated frames 36b so as to snake to avoid the respective wire driving parts 31 as shown in FIGS. 13 to 16.

The other formations are the same as in the second embodiment.

According to this embodiment, the number of the wire driving parts 31 contained in any cross-section of the insertable part 11 is one or less and the insertable part 11 can have a small outside diameter.

The other operations and effects are the same as in the second embodiment.

In the present invention, for example, only one of the four wire driving parts 31 may be arranged in a different position in the axial direction of the insertable part 11 and, in the case of curving the curvable part 16 in the vertical or horizontal direction only, two wire driving parts may be provided and arranged in positions different from each other in the axial direction of the insertable part 11.

As explained above, according to the second and third embodiments, there is an effect that, since at least one curving driving means is arranged in a different position in the axial direction of the insertable part, even if a plurality of curving driving means are provided in the insertable part, the insertable part have a small outside diameter.

Figure 17:
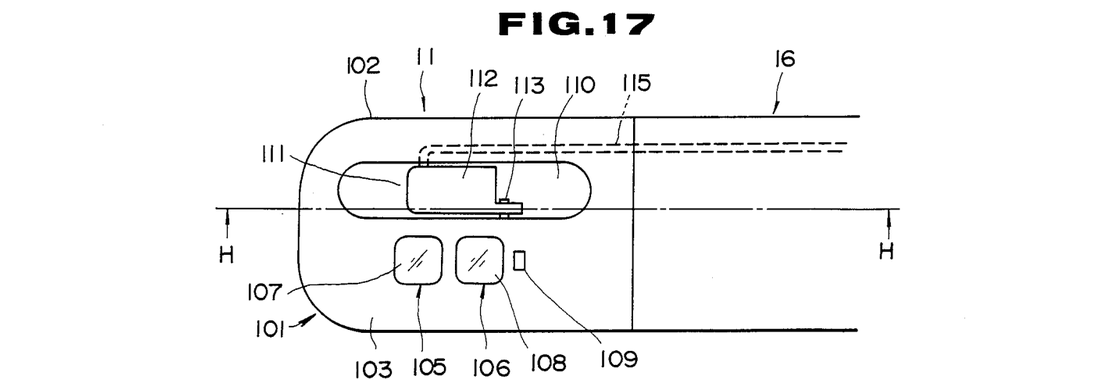
FIG. 17 is a plan view of a tip part.
Figure 18:
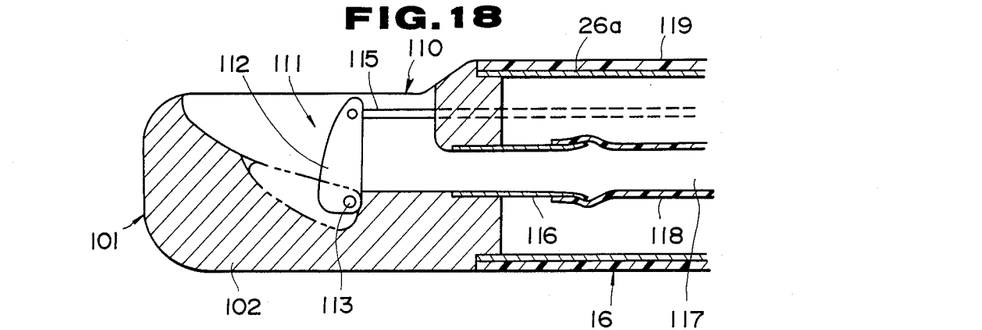
FIG. 18 is a sectioned view on line H—H in FIG. 17.
Figure 19:
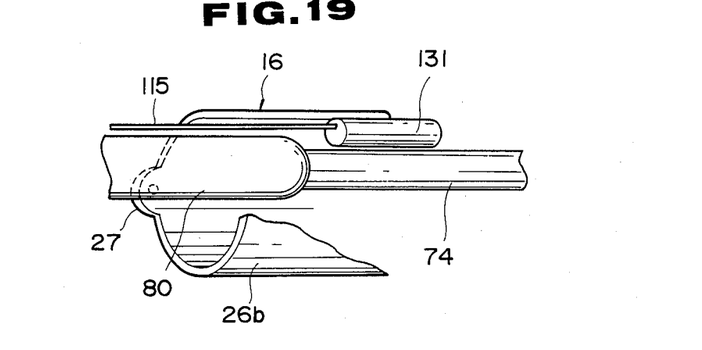
FIG. 19 is a perspective view showing the vicinity of a curvable part.

FIGS. 17 to 19 show the fourth embodiment of the present invention.

This embodiment is an example of a side viewing type endoscope.

As shown in FIG. 18, a tip part 101 of an insertable part 11 has a substantially columnar rigid tip body 102 of a curved surface at the tip. A flat part 103 incised in the axial direction of the insertable part 11 is formed on one side of this tip body 102 and is provided on one side with an illuminating window 105 and an observing window 106 from the tip side in the axial direction of the insertable part 11 as shown in FIG. 17 on this flat surface part. A treating tool outlet 110 communicating with a treating tool channel is formed on the other side adjacent to the above mentioned illuminating window 105 and observing window 106. The above mentioned illuminating window 105 is fitted with a light distributing lens 107 inside which a light guide 75 is provided. The above mentioned observing window 106 is fitted with an objective optical system 108. The tip surface of an image guide 74 is arranged in the image forming position of this objective optical system 108. The above mentioned tip body 102 is provided with an air and water feeding nozzle 109 opening toward the observing window 106. An air and water feeding tube forming an air and water feeding channel is connected to this air and water feeding nozzle 109, is inserted through the insertable part 11, operating part 12 and universal cord 14 and is connected to a connector 14.

A treating tool raising stand 112 forming a treating tool raising device 111 is arranged within the above mentioned treating tool outlet 110 and is rotatable on the tip side a rotary shaft 113 on the rear end side as a center. A wire 115 for driving the treating tool raising device is connected at one end to the tip side of this treating tool raising stand 112.

As shown in FIG. 18, a channel pipe 116 is fitted to the rear end part of a through hole communicating with the treating tool outlet 110 formed in the tip body 102 and is formed in the rear end part to be tapered to be of a longer diameter on the side of the rear end to which a channel tube 118 forming a treating tool channel 117 is externally fitted in the tip part and is connected. This channel tube 118 is inserted through the insertable part 11 and is connected to a treating tool inserting port not illustrated provided in the operating part 12.

An articulated frame 26a at the foremost end is connected to, the above mentioned tip body 102 at the rear end. THe articulated frames 26 including this articulated frame 26a are coated with a curvable tube 119.

As shown in FIG. 19, a wire driving part 131 as a driving means driving the treating tool raising device to pull the above mentioned wire 115 is fitted, for example, to the inner peripheral surface of the articulated frame 26b at the rearmost end. The same as in the wire driving part 31 of the first embodiment, a vibration wave motor is used for this wire driving part 131.

Also, the same as in the first embodiment, the image guide 74 within the curvable part 16 is coated with the protective tube 80. This protective tube 80 is set in the entire length to be closer at the rear end to the operating part 12 side than the connecting piece 27 of the articulated frame 26b at the rearmost end when the curvable part 16 is freely curved. Also, the above mentioned wire driving part 131 is arranged at a distance secured in the axial direction from the rear end of the protective tube 80 when the curvable part is freely curved. That is to say, the above mentioned wire driving part 131 is arranged to be closer to the operating part side than the position in which the image guide 74 and protective tube 80 become smaller in outside diameter.

In this embodiment, as a means of driving the curvable part 16, four wire driving parts 31a to 31d which are vibration wave motors may be provided within the insertable part 12 or a curving operation knob may be provided on the operating part 12. When the wire driving parts 31a to 31d are used as a means of driving the curvable part 16, the same as in the first embodiment, it is desirable that these wire driving parts 31a to 31d are arranged also to be closer to the operating part 12 side than the position in which the image guide 74 and protective tube 80 become smaller in outside diameter. Also, the same as in the second or third embodiment, it is desirable that one wire driving part of the wire driving parts 31a to 31d and wire driving part 131 is arranged in a position in the axial direction of the insertable part 12 which is different from the other wire driving parts.

The other formations are the same as in the first embodiment.

In this embodiment, when the wire 115 is pulled by the above mentioned wire driving part 131, the treating tool raising stand 112 will be rotated to the state indicated by the solid line from the state indicated by the two-point chain line in FIG. 18 and thereby the treating tool inserted through the treating tool channel 117 will be able to be raised on the tip side.

In this embodiment, as the thick part of the image guide 74 coated with the protective tube 80 and the wire driving part 131 are not overlapped with each other in any cross-section in the axial direction of the insertable part, the maximum content area of the insertable part 11 will be smaller than when the above mentioned wire driving part 131 is provided in the rear end part of the curable part 16 so as to overlap with the above mentioned protective tube 80.

The other operations and effects are the same as in the first embodiment.

The present invention is not limited to the above mentioned respective embodiments, the observing means is not limited to use an image guide, a solid state imaging device may be provided in the tip part and an object image imaged by this solid state imaging device may be displayed in a monitor to be observed. In such a case, within the curvable part, the signal line connected to the solid state imaging device may be coated with a protective tube and a driving part for driving the curvable part or for driving the treating tool raising device may be provided to be closer to the operating part side than the rear end of this protective tube.

In this invention, it is apparent that working modes different in a wide range can be formed on the basis of this invention without deviating from the spirit and scope of the invention. This invention is not restricted by its specific working mode except being limited by the appended claims.

What is claimed is:

1. An endoscope comprising:
   an elongate insertable part having an observing window in a tip part;
   a observing means for observing an object by receiving a light entering through said observing window;
   contents which are contained within said insertable part, at least one of said contents varies in outside diameter so as to be smaller in diameter on a promixal side;
   driven parts provided in said insertable part; and
   a driving means driving said driven parts and arranged to be closer to a proximal end side than a position in which said contents vary in outside diameter within said insertable part.

2. An endoscope comprising:
an elongate insertable part having an observing window in a tip part;
an observing means for observing an object by receiving a light entering through said observing window;
contents which are contained within said insertable part, at least one of said contents varies in outside diameter so as to be smaller in diameter on a proximal end side;
a curvable part provided to be curvable in said insertable part; and
driving means driving said curvable part to be curved and arranged to be closer to a proximal end side than a position in which said contents vary in outside diameter within said insertable part.

3. An endoscope comprising:
an elongate insertable part having an observing window in a tip part;
an observing means for observing an object by receiving a light entering through said observing window;
a treating tool channel formed within said insertable part;
a treating tool raising device provided in a treating tool channel opening part in the tip part of said insertable part and raising on a distal side of a treating tool inserted through said treating tool channel;
contents which are contained within said insertable part, at least one of said contents varies in outside diameter so as to be smaller in diameter on a proximal end side; and
driving means driving said treating tool raising device and arranged to be closer to a proximal end side than a position in which said contents vary in outside diameter within said insertable part.

4. An endoscope comprising:
an elongate insertable part having an observing window in a tip part;
an observing means for observing an object by receiving a light entering through said observing window;
a curvable part provided on said insertable part;
a plurality of driving means which are provided within said insertable part and are to drive said curvable part to be curved and at least one of which is arranged in a different position in an axial direction of the insertable part from the other driving means; and
contents which are contained within said insertable part, at least one of said contents varies in outside diameter so as to be smaller in diameter on a proximal end side, said plurality of driving means being arranged to be closer to the proximal end side that a position in which said contents vary in outside diameter within said insertable part.

5. An endoscope according to claim 1 or 3 wherein said observing means has an objective optical system provided in the tip part of said insertable part, an eyepiece part provided on a proximal end side of said insertable part and an image transmitting means, transmitting to said eyepiece part an object image formed by said objective optical system and said image transmitting means is one of said contents.

6. An endoscope according to claim 5 wherein said insertable is provided with a curvable part and said image transmitting means is coated with a protective tube in the part corresponding to said curvable part and varies in outside diameter to be smaller in diameter on the proximal end side.

7. An endoscope according to claim 2 or 4 wherein said observing means has an objective optical system provided in the tip part of said insertable part, an eyepiece part provided on a proximal end side of said insertable part and an image transmitting means transmitting to said eyepiece part an object image formed by said objective optical system and said image transmitting means is one of said contents.

8. An endoscope according to claim 7 wherein said image transmitting means is coated with a protective tube in the part corresponding to said curvable part and varies in outside diameter so as to be smaller in diameter on the proximal end side in the rear end part of said coating tube.

9. An endoscope according to claim 4 wherein said observing means has an objective optical system provided in the tip part of said insertable part, an eyepiece part provided on a proximal end side of said insertable part and an image transmitting means transmitting to said eyepiece part an object image formed by said objective optical system.

10. An endoscope according to claim 1 or 3 wherein said insertable part further has an illuminating window in the tip part and is provided with an illuminating light transmitting means transmitting an illuminating light to said illuminating window and being one of said contents.

11. An endoscope according to claim 10 wherein insertable part is provided with a curvable part and said illuminating light transmitting means is coated with a protective tube in part corresponding to said curvable part and varies in outside diameter so as to be smaller in the diameter on a proximal end side in the rear end part of said coating tube.

12. An endoscope according to claim 2 or 4 wherein said insertable part further has an illuminating window in the tip part and is provided with an illuminating light transmitting means transmitting an illuminating light to said illuminating window and being one of said contents.

13. An endoscope according to claim 12 wherein said illuminating light transmitting means is coated with a protective tube in the part corresponding to said curvable part and varies in outside diameter so as to be smaller in diameter on a proximal end side in a proximal end part of said coating tube.

14. An endoscope according to claim 4 wherein said insertable part further has an illuminating window in the tip part and is provided with an illuminating light transmitting means transmitting an illuminating light to said illuminating window.

15. An endoscope according to claim 1, 2, 3, or 4 wherein said driving means is a vibration wave motor.

16. An endoscope according to claim 2, or 4 wherein said curvable part has a plurality of cylinder members connected so as to be curvable as a whole, a wire is connected at one end to the cylinder member at a foremost end and said driving means is connected to said wire at another end to pull said wire.

17. An endoscope according to claim 16 wherein said curvable part is curvable in at least two directions, at least two of said wires are provided, said respective wires are connected each at one end to said foremost end cylinder member in positions substantially at regular intervals from each other in a peripheral direction and said driving means are provided in response to said respective wires and in positions substantially at regular intervals from each other in the peripheral direction in an inner peripheral part of rearmost end cylinder member.

18. An endoscope according to claim 17 wherein four driving means are provided, two of said four driving means are arranged in same positions in the axial direction of the insertable part and the remaining two driving means are arranged in different positions in the axial direction of the insertable part from the positions of said two driving means.

19. An endoscope according to claim 18 wherein at least one of said contents is arranged so as to snake to avoid said plurality of driving means arranged in front and rear in the axial direction.

20. An endoscope according to claim 17 wherein said respective driving means are arranged in respectively different positions in an axial direction of the insertable part.

21. An endoscope according to claim 20 wherein at least one of said contents is arranged so as to snake to avoid said plurality of driving means arranged in front and rear in the axial direction.

22. An endoscope according to claim 3 wherein said treating tool raising device has a treating tool raising stand provided in treating tool channel opening part and rotatable on the tip side with a rotary shaft on a proximal end side as a center, a wire is connected at one end to said treating tool raising stand and said driving means is connected to said wire at another end and pulls said wire.

* * * * *